(12) United States Patent
Ou et al.

(10) Patent No.: US 11,446,198 B2
(45) Date of Patent: Sep. 20, 2022

(54) LOWER SUPPORT TYPE REHABILITATION DEVICE FOR FINGERS

(71) Applicant: SOUTHERN TAIWAN UNIVERSITY OF SCIENCE AND TECHNOLOGY, Tainan (TW)

(72) Inventors: Yang-Kun Ou, Tainan (TW); Chun-Chih Chen, Tainan (TW); Yu-Ling Wang, Tainan (TW); Yu-Ning Huang, Tainan (TW)

(73) Assignee: Southern Taiwan University of Science and Technology, Tainan (TW)

( * ) Notice: Subject to any disclaimer, the term of this patent is extended or adjusted under 35 U.S.C. 154(b) by 951 days.

(21) Appl. No.: 16/218,740

(22) Filed: Dec. 13, 2018

(65) Prior Publication Data
US 2020/0129361 A1    Apr. 30, 2020

(30) Foreign Application Priority Data
Oct. 24, 2018 (TW) ................................. 107137606

(51) Int. Cl.
*A61H 1/02* (2006.01)
*A63B 21/00* (2006.01)
(Continued)

(52) U.S. Cl.
CPC ....... *A61H 1/0288* (2013.01); *A63B 21/4019* (2015.10); *A61B 5/1107* (2013.01);
(Continued)

(58) Field of Classification Search
CPC ............ A61H 1/0288; A61H 2201/165; A61H 2205/067; A61H 2201/1207;
(Continued)

(56) References Cited

U.S. PATENT DOCUMENTS

| 2012/0029399 A1* | 2/2012 | Sankai | A61H 1/0288 |
| | | | 601/40 |
| 2013/0072829 A1* | 3/2013 | Fausti | A63B 23/16 |
| | | | 601/40 |

(Continued)

FOREIGN PATENT DOCUMENTS

| TW | I620558 B | 4/2018 |
| TW | I626040 B | 6/2018 |

*Primary Examiner* — Quang D Thanh
(74) *Attorney, Agent, or Firm* — Rosenberg, Klein & Lee (57) ABSTRACT

A lower support type rehabilitation device for fingers includes a cover plate having a hand covering portion and a plurality of through holes. A plurality of finger supports are disposed on the hand covering portion, each having a first finger base, a second finger base pivotally connected to the first finger base, two side arms and a beam disposed on the first finger base. A traction device is disposed on the hand covering portion and has a first processing module, a plurality of driving modules electrically connected to the first processing module, a plurality of pulling ropes connected to the plurality of driving modules and a plurality of pressure sensors electrically connected to the first processing module. Each of the plurality of pulling ropes passes through one of the plurality of through holes for fixing to the beam of the first finger base.

10 Claims, 7 Drawing Sheets

(51) Int. Cl.
  *A61B 5/22* (2006.01)
  *A61B 5/11* (2006.01)
(52) U.S. Cl.
  CPC ............ *A61B 5/225* (2013.01); *A61B 2505/09* (2013.01); *A61H 2201/165* (2013.01); *A61H 2205/067* (2013.01); *A63B 21/00178* (2013.01)
(58) Field of Classification Search
  CPC .......... A61H 2201/5071; A61H 1/0274; A63B 21/4019; A63B 21/00178; A61B 5/1107; A61B 5/225; A61B 2505/09; A61F 5/103; A61F 2005/0155
  See application file for complete search history.

(56) References Cited

U.S. PATENT DOCUMENTS

| | | | |
|---|---|---|---|
| 2017/0168565 A1* | 6/2017 | Cohen | A61B 5/0022 |
| 2017/0266075 A1* | 9/2017 | Becchi | A63B 23/16 |
| 2018/0177666 A1* | 6/2018 | Tsui | A61H 1/0288 |

* cited by examiner

LOWER SUPPORT TYPE REHABILITATION DEVICE FOR FINGERS

BACKGROUND OF THE INVENTION

1. Field of the Invention

The present invention relates to a lower support type rehabilitation device for fingers which has plural finger supports and plural pressure sensors to assist finger movement of a stroke patient by supporting the bottom side of each finger and detect the pressure on the patient's fingers for avoiding finger injury due to overstretching.

2. Description of Related Art

Strokes, including the ischemic stroke caused by vascular obstruction and the hemorrhagic stroke caused by bleeding, result in abnormal brain function and are also the leading causes of death and physical disability in the global population. In Taiwan, one person dies of the stroke every 40 minutes, and in human life, the incidence of stroke is about one-sixth. According to the Taiwan Stroke Registry, the rates of disability in the stroke patients after a month, 3 months, and half a year of stroke are 61.2%, 55.58%, and 51.72%, respectively. The symptoms of disability include the inability to move the unilateral limbs, the loss of the unilateral body sensation, the inability to speak or understand other people's words, the vertigo, and the loss of the unilateral vision.

Stroke patients with disability, especially the physical disability, are unable to take care of their own lives and often need the assistance of others to carry out normal activities. Accordingly, the assistive devices or training devices for assisting the activities of stroke patients were developed. For instance, the Taiwan patent No. TWI626040 (B), issued on 11 Jun. 2018, has disclosed a "dynamic hand assistive device" to assist patients in training their hand muscles. It comprises a wrist unit for connecting to a thumb unit, an index finger unit, a middle finger unit, a ring finger unit and a small finger unit respectively. The aforementioned index finger unit, the middle finger unit, the ring finger unit and the small finger unit all include an elastic wire, and the wrist unit, the thumb unit and the index finger unit are connected by three linkages.

Furthermore, the Taiwan patent No. TWI620558 (B), issued on 11 Apr. 2018, has disclosed a wearable hand rehabilitation system. It can be used with sliding rail connecting rods, wire pulleys, and wire gathering columns. When a user put on the wearable hand rehabilitation system, the user could move or rotate his/her arm to make his/her five fingers to grab something. The wearable hand rehabilitation system can be used to test the hand rehabilitation condition of the user. However, the abovementioned assistive devices can only fix or pull the upper side of the fingers to move, so the muscles of the patient's fingers are not completely relaxed and subject to great pressure. Therefore, there is a need to provide an assistive device that reduces the pressure on the patient's hand when wearing to facilitate the rehabilitation.

SUMMARY OF THE INVENTION

In view of the above-mentioned problems, the object of the present invention is to provide a lower support type rehabilitation device for fingers which has plural finger supports to support the bottom side of each finger of a patient, plural pressure sensors and plural pulling ropes to assist the patient's fingers to perform the stretching action, so that the patients can gradually move his or her fingers actively.

Disclosed herein is a lower support type rehabilitation device for fingers. It comprises a cover plate having a hand covering portion and a plurality of through holes disposed on the hand covering portion; a plurality of finger supports disposed at a bottom of the hand covering portion and each having a first finger base, a second finger base pivotally connected to the first finger base, and two side arms respectively disposed on two sides of the second finger base, wherein the first finger base is provided with a beam; and a traction device disposed on the hand covering portion of the cover plate and having a first processing module, a plurality of driving modules electrically connected to the first processing module, a plurality of pulling ropes connected to the plurality of driving modules and a plurality of pressure sensors electrically connected to the first processing module, wherein each of the plurality of pulling ropes passes through one of the plurality of through holes for fixing to the beam of the first finger base.

According to an embodiment of the present invention, the hand covering portion comprises an arm covering portion, a hand back covering portion connected to the arm covering portion, a first finger covering portion connected to the hand back covering portion, and a second finger covering portion connected to the hand back covering portion.

According to an embodiment of the present invention, five finger supports are provided, one of which is disposed at a bottom of the first finger covering portion and the other four are disposed at a bottom of the second finger covering portion.

According to an embodiment of the present invention, the cover plate is further provided with a plurality of motor fixed brackets and a plurality of pulling rope fixed brackets on the hand covering portion.

According to an embodiment of the present invention, the first finger base is provided with a first lower pallet connected to the beam. The first lower pallet and the beam define a ring-like structure.

According to an embodiment of the present invention, the second finger base is provided with a second lower pallet and two side plates respectively disposed on two sides of the second lower pallet.

According to an embodiment of the present invention, each of the two side arms has a first end connected to each of the two side plates and a second end connected at the bottom of the first finger covering portion or at the bottom of the second finger covering portion.

According to an embodiment of the present invention, each of the plurality of driving modules of the traction device comprises a driving motor and a swing arm connected to the driving motor for further connecting each of the plurality of pulling ropes.

According to an embodiment of the present invention, an active processing device is further provided and comprises a second processing module electrically connected to the first processing module and a plurality of bending sensors electrically connected to the second processing module.

DETAILED DESCRIPTION OF THE PREFERRED EMBODIMENT

Hereinafter, an exemplary embodiment of the present invention will be described in detail with reference to the accompanying drawings.

As showed in FIGS. 1-5, a lower support type rehabilitation device for fingers according to the present invention is disclosed. It comprises a cover plate (1), a plurality of finger supports (2) and a traction device (3).

Figure 1:
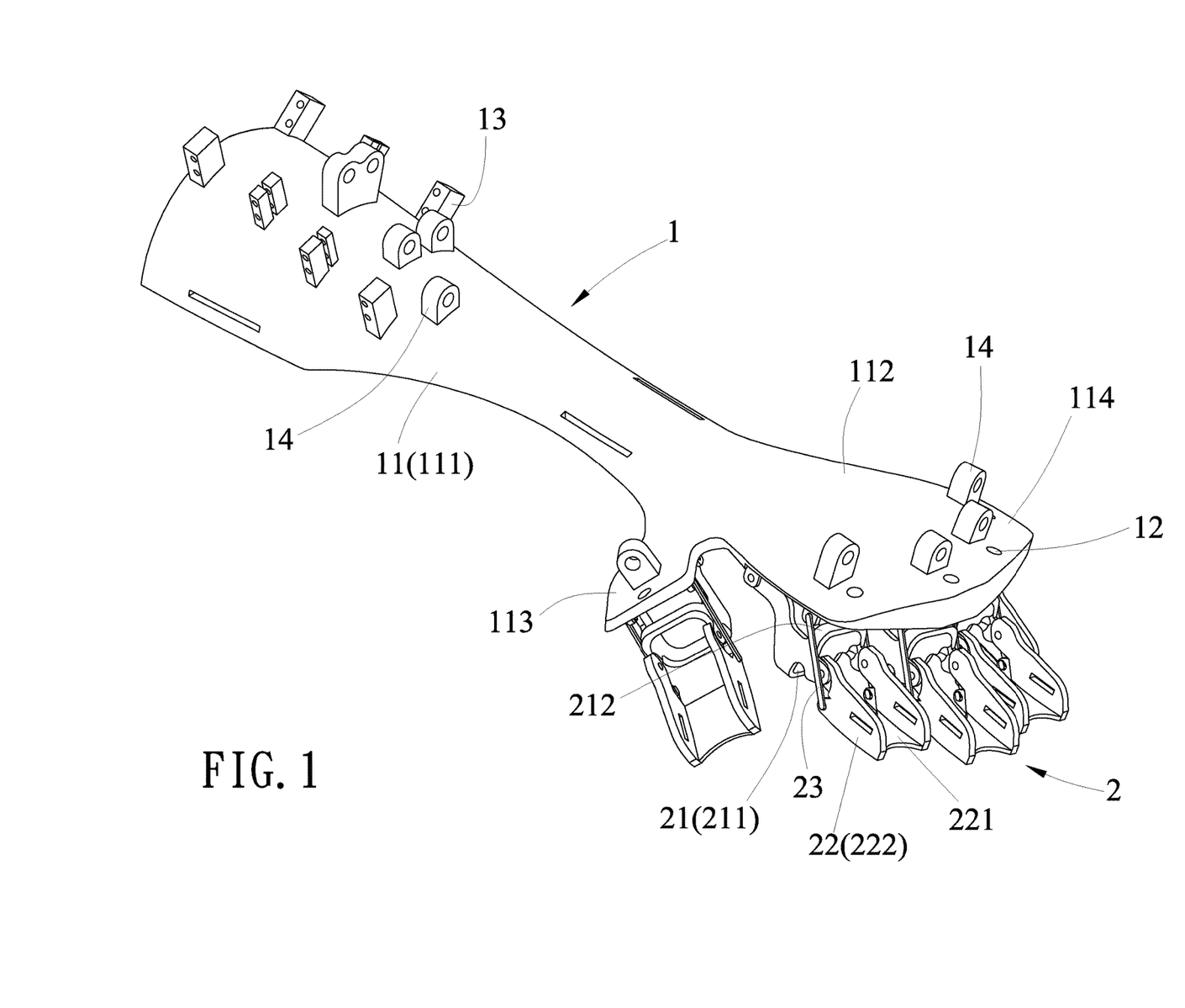
FIG. 1 is a stereogram showing a lower support type rehabilitation device for fingers according to the present invention.

The cover plate (1) has a hand covering portion (11), a plurality of through holes (12) disposed on the hand covering portion (11), and a plurality of motor fixed brackets (13) and a plurality of pulling rope fixed brackets (14) disposed on the hand covering portion (11). The hand covering portion (11) comprises an arm covering portion (111), a hand back covering portion (112) connected to the arm covering portion (111), a first finger covering portion (113) connected to the hand back covering portion (112), and a second finger covering portion (114) connected to the hand back covering portion (112).

Figure 4:
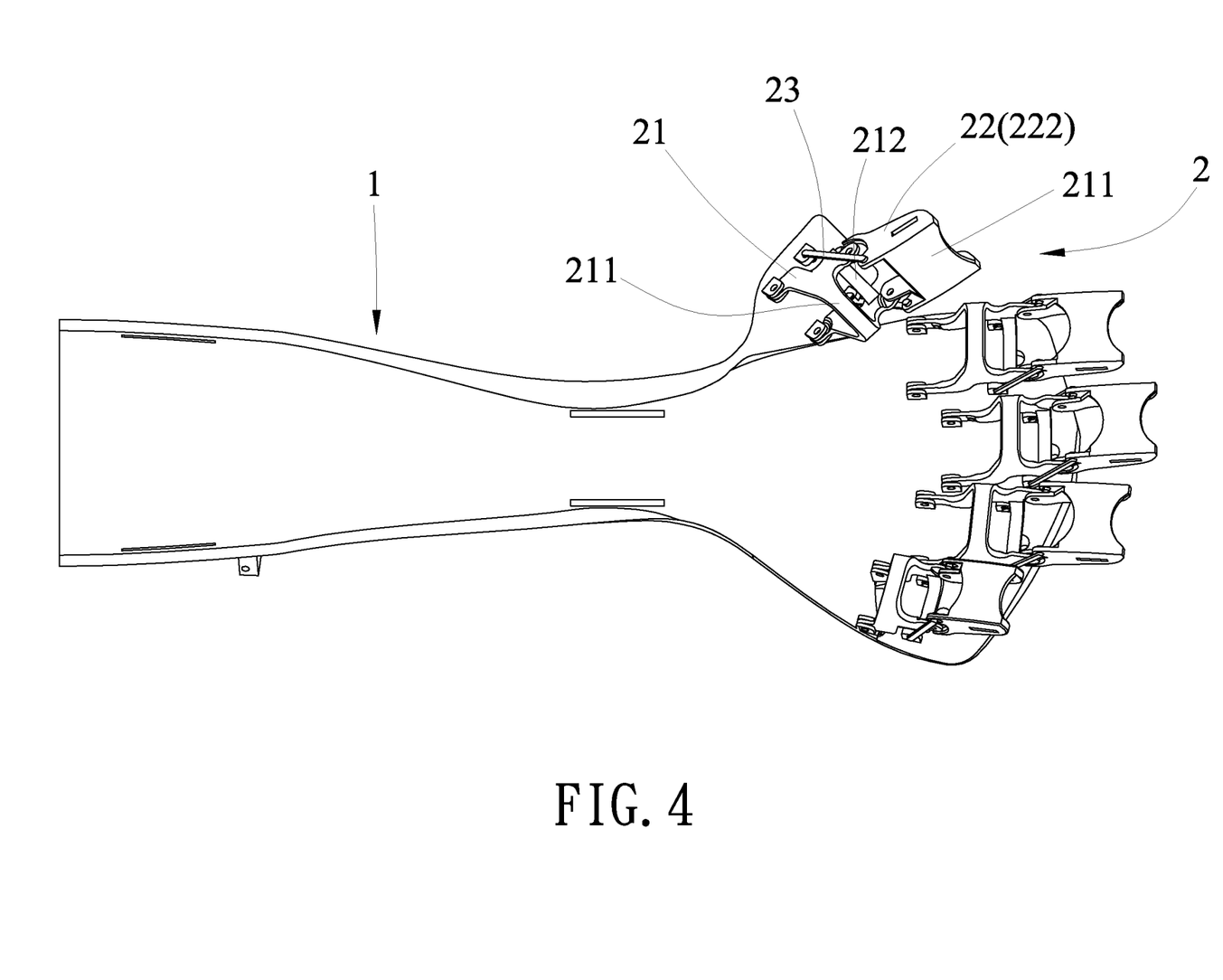
FIG. 4 is a bottom view showing a plurality of finger supports according to the present invention.
Figure 5:
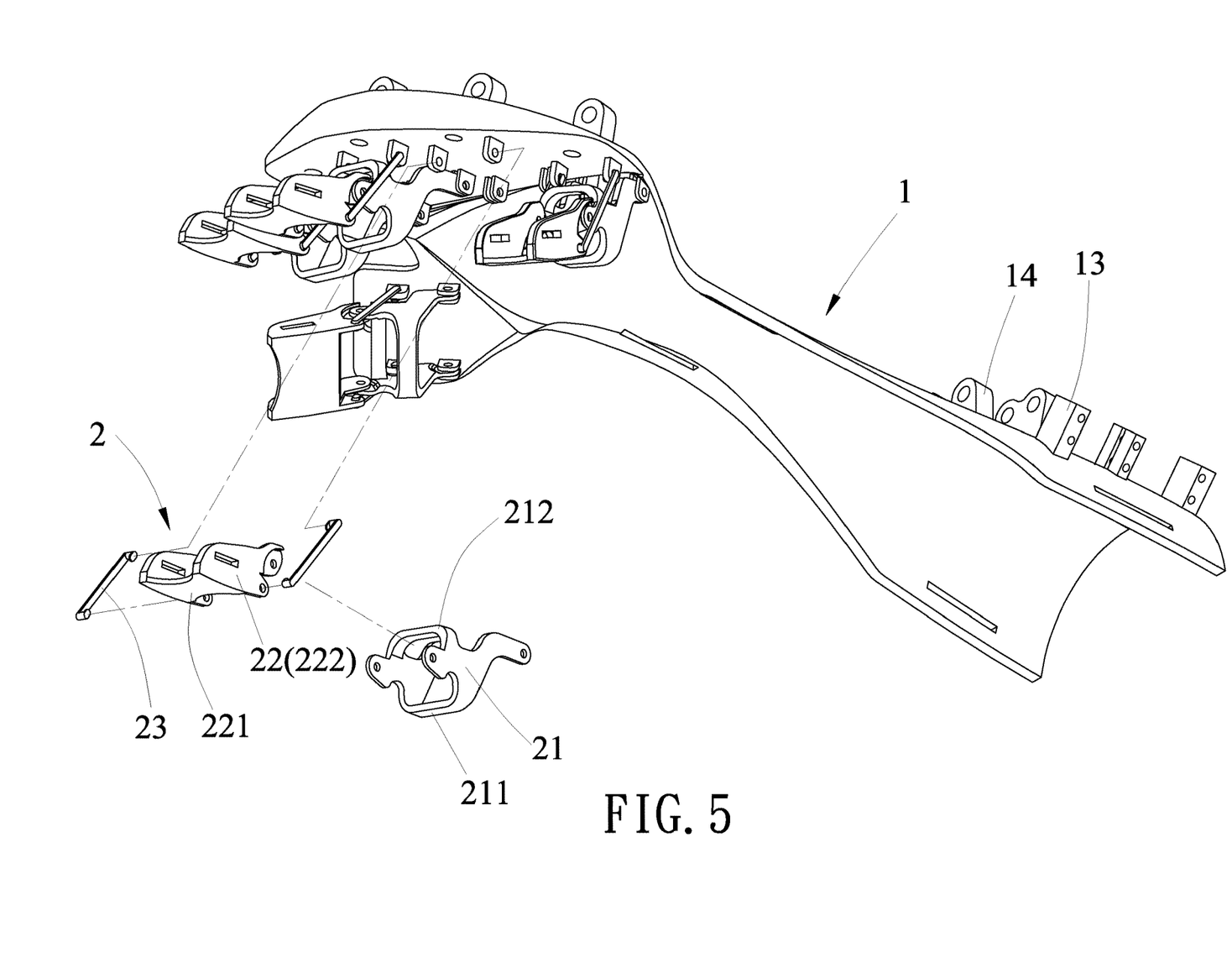
FIG. 5 is an exploded view showing a finger support according to the present invention.

Five finger supports (2) are provided and disposed at a bottom of the hand covering portion (11), one of which is disposed at a bottom of the first finger covering portion (113) of the hand covering portion (11) and the other four are disposed at a bottom of the second finger covering portion (114) of the hand covering portion (11). Each of the finger supports (2) has a first finger base (21), a second finger base (22) pivotally connected to the first finger base (21), and two side arms (23) respectively disposed on two sides of the second finger base (22). Furthermore, each of the first finger bases (21) is provided with a first lower pallet (211) and a beam (212) connected to the first lower pallet (211). The first lower pallet (211) and the beam (212) define a ring-like structure for insertion of a finger. Each of the second finger bases (22) is provided with a second lower pallet (221) and two side plates (222) respectively disposed on two sides of the second lower pallet (221). Each of the two side arms (23) has a first end connected to each of the two side plates (222) of each of the second finger bases (22) and a second end connected at the bottom of the first finger covering portion (113) or at the bottom of the second finger covering portion (114).

Figure 2:
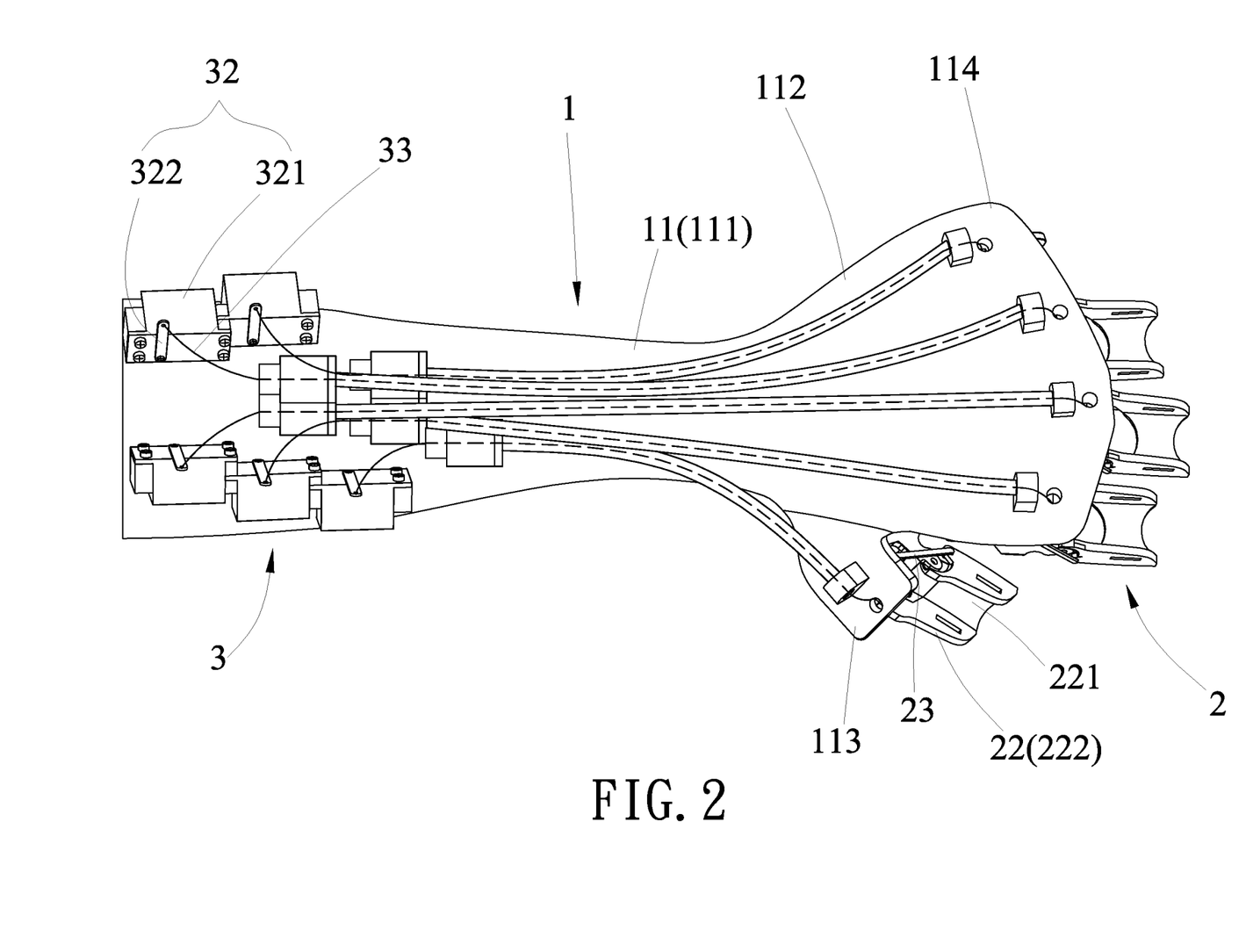
FIG. 2 is a stereogram showing a traction device according to the present invention.

The traction device (3) is disposed on the hand covering portion (11) of the cover plate (1) and comprises a first processing module (31), a plurality of driving modules (32) electrically connected to the first processing module (31), a plurality of pulling ropes (33) connected to the plurality of driving modules (32) and a plurality of pressure sensors (34) electrically connected to the first processing module (31). Each of the plurality of driving modules (32) comprises a driving motor (321) and a swing arm (322) connected to the driving motor (321) for further connecting each of the plurality of pulling ropes (33), and each of the plurality of pulling ropes (33) passes through one of the plurality of through holes (12) for fixing to the beam (212) of the first finger base (21).

Figure 3:
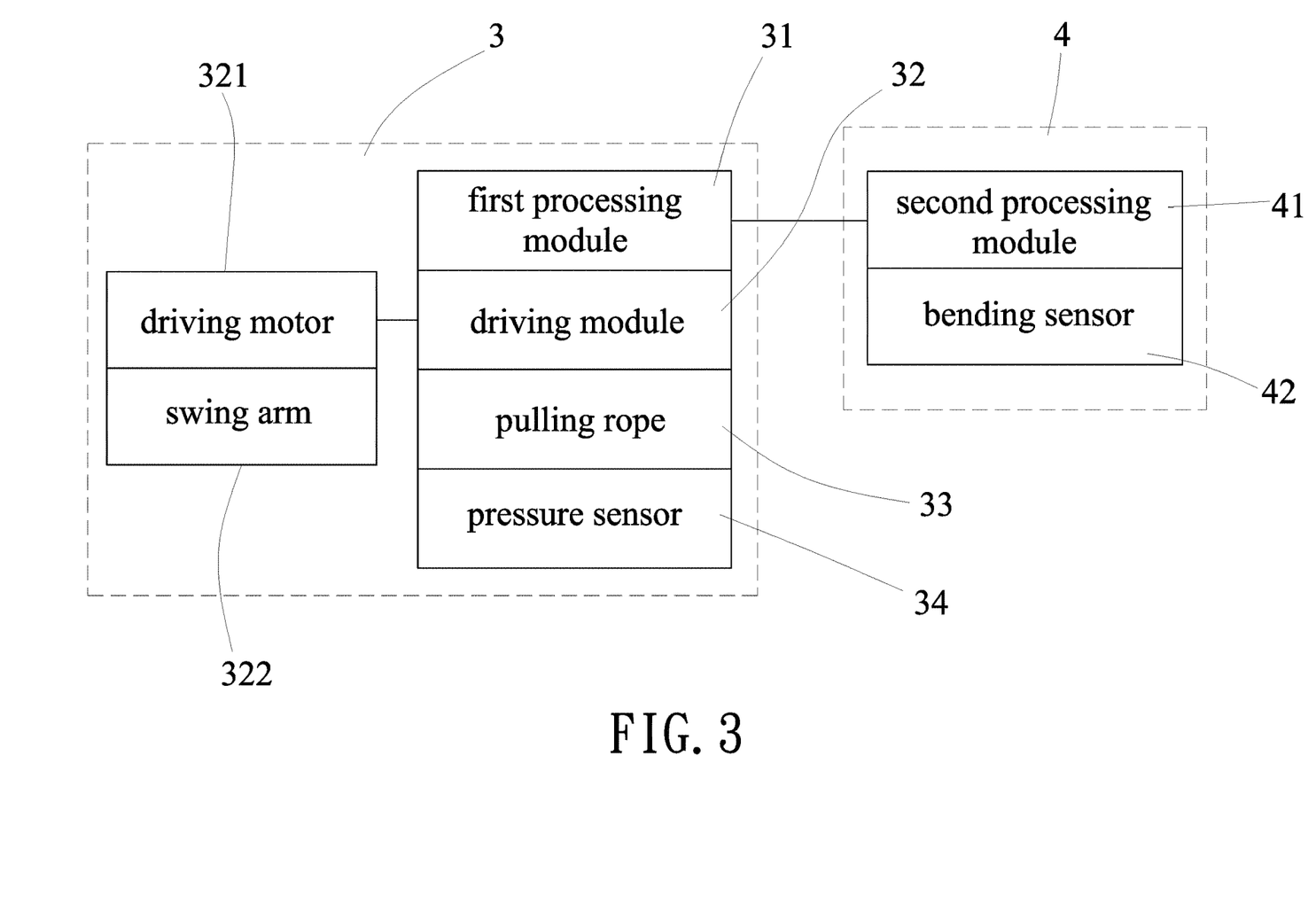
FIG. 3 is a block diagram showing a traction device and an active processing device according to the present invention.

The lower support type rehabilitation device for fingers of the present invention further comprises an active processing device (4), and the active processing device (4) comprises a second processing module (41) electrically connected to the first processing module (31) and a plurality of bending sensors (42) electrically connected to the second processing module (41).

In addition, the following specific examples further clarify but are not limited to the scope of the invention.

Referring to FIGS. 1-5, the lower support type rehabilitation device for fingers guides the rehabilitation person's hand to perform stretching and bending actions and assists the metacarpophalangeal joint (MCP Joint) to perform 90-100 degrees of activities, the proximal interphalangeal joint (PIP Joint) to perform 90 degree of activities, and the distal interphalangeal joint (DIP Joint) to perform 90 degree of activities.

In a practical use, the hand covering portion (11) of the cover plate (1) is covered on an affected side of a rehabilitator's hand. The arm covering portion (111) as well as the hand back covering portion (112) are respectively covered on an arm portion and a hand back portion of the rehabilitator's hand, and the first finger covering portion (113) and the second finger covering portion (114) are respectively covered on a thumb and the other four fingers. After the thumb and the other four fingers respectively pass through the five ring-like structures defined by the first lower pallets (211) and the beams (212) of the five finger supports (2) and place on the first finger bases (21) and the second finger bases (22), the first lower pallets (211) of the first finger bases (21) provide support to carry the proximal phalanges of the five fingers, and the second lower pallets (221) of the second finger bases (22) provide support to carry the distal phalange of the five fingers. In such a case, the rehabilitator can easily place his or her fingers on the first finger bases (21) and the second finger bases (22).

Figure 6:
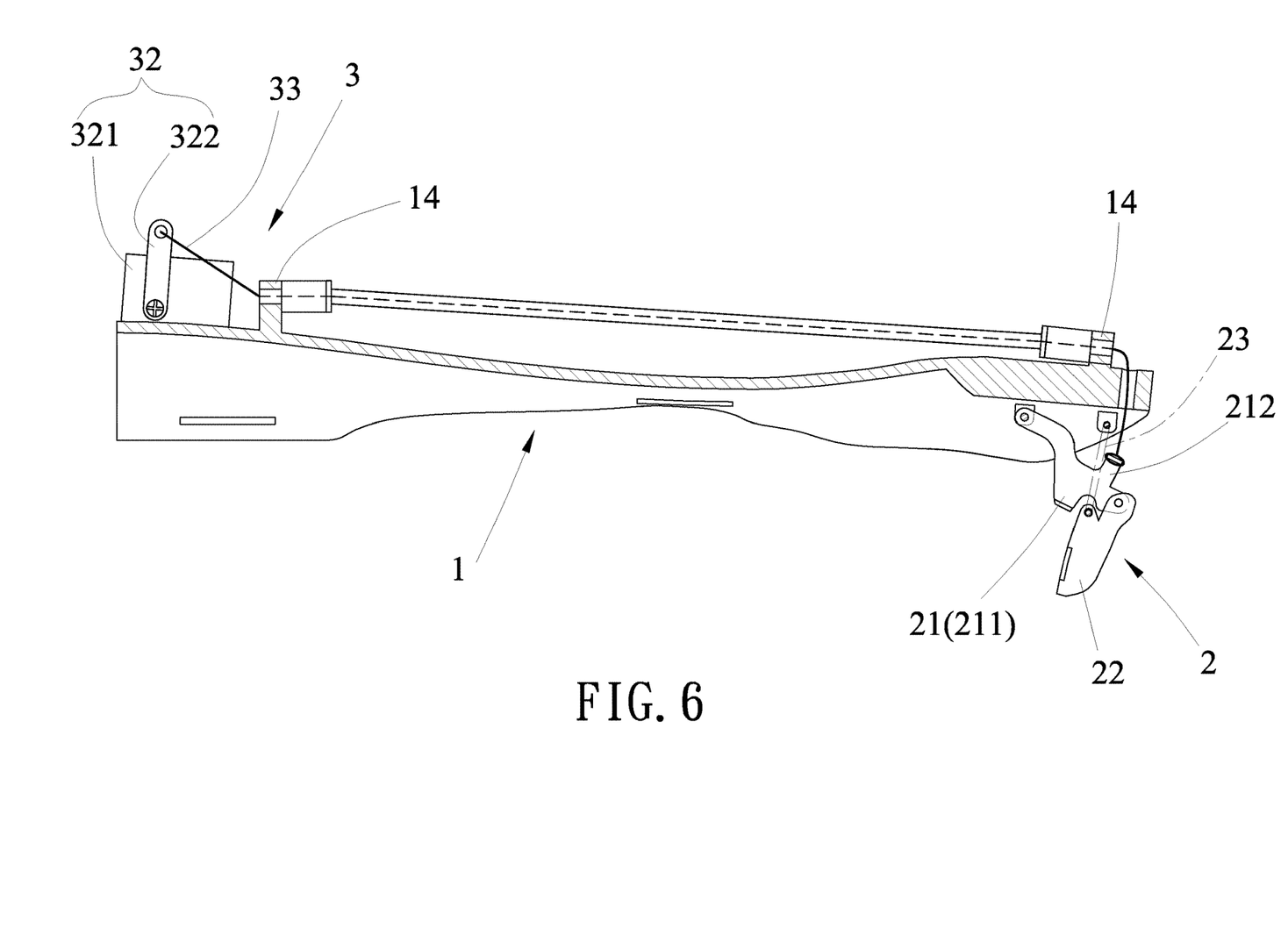
FIG. 6 is a first schematic diagram showing a traction device in actuation according to the present invention.
Figure 7:
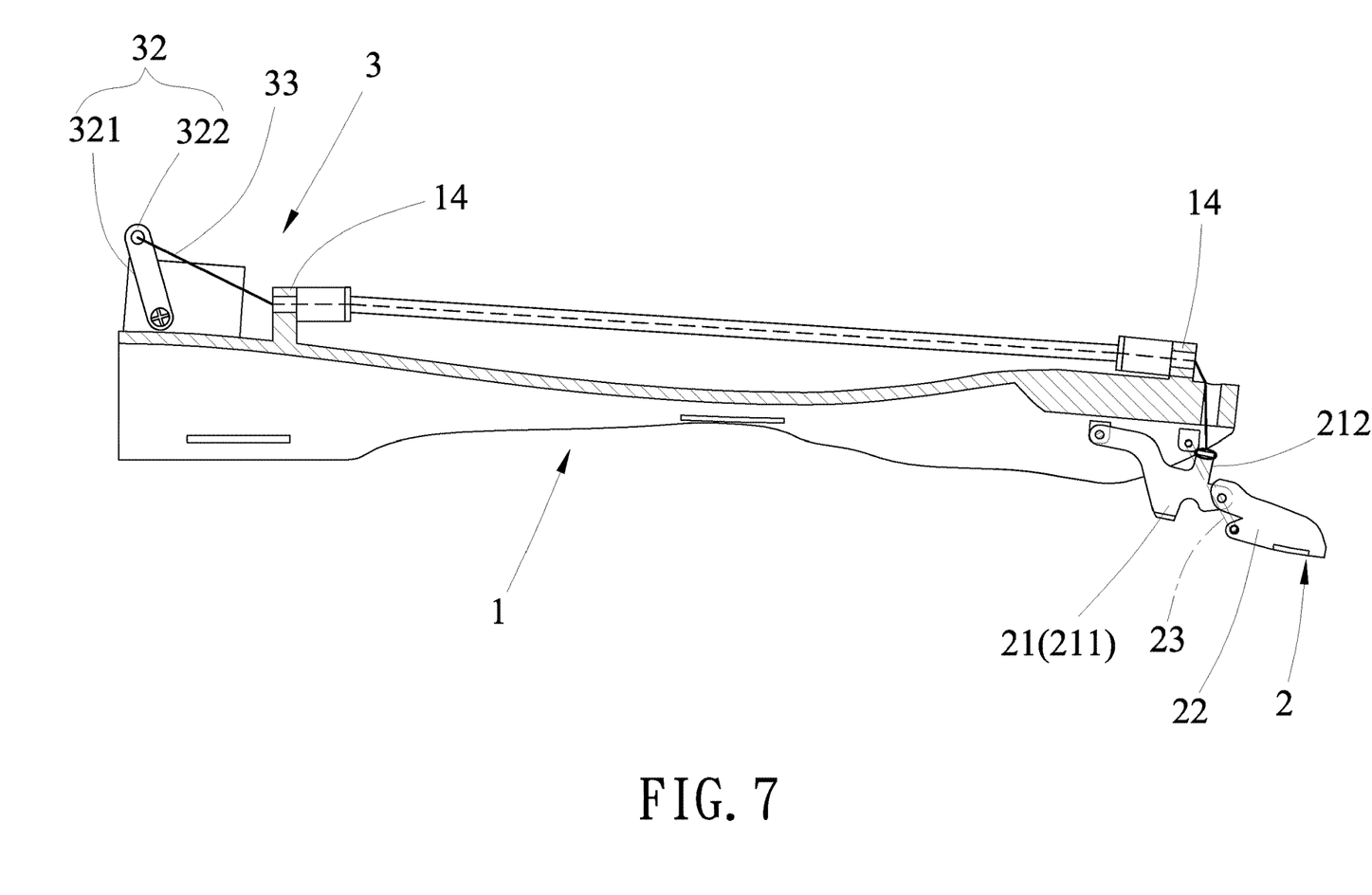
FIG. 7 is a second schematic diagram showing a traction device in actuation according to the present invention.

During rehabilitation, the rehabilitator can directly bend his or her fingers inwardly to make a first or try to stretch out the fingers by himself/herself or by the traction device (3) to assist to stretch out the fingers. Referring to FIG. 6 and FIG. 7, the first processing module (31) of the traction device (3) transmits commands to the driving modules (32) which has five driving motors (321) fixed on the motor fixed brackets (13) and five swing arms (322). Each finger corresponds to one driving motor (321) and one swing arm (322). After the driving modules (32) receives the commands, the driving motors (321) of the driving modules (32) start to operate and drive the swing arms (322) to rotate. When the swing arm (322) rotates upwardly, the pulling ropes (33) having one ends attached to the swing arm (322) is pulled. The other ends of the pulling ropes (33) are fixed to the beam (212) of the first finger bases (21) through pipelines provided on the pulling rope fixed brackets (14). Accordingly, when pulled by the swing arm (322), the pulling ropes (33) pulls the beam (212) to drive the first finger bases (21) and the second finger bases (22) pivotally connected to the first finger bases (21) to move upward and toward the back of the hand, and the side arms (23) disposed on two sides of the two side plates (222) of the second finger bases (22) are also pulled to rotate upwardly. In such a case, the rehabilitator's fingers on the affected side can be trained for reconstruction.

Additionally, the pressure sensors (34) of the traction device (3) continuously detect the flexural tension of the rehabilitator's fingers and transmit the flexural tension information to the first processing module (31). When the first processing module (31) determines that the flexural tension exerted on the rehabilitator's fingers is greater than a predetermined value, the first processing module (31) transmits commands to the driving modules (32) to stop the driving motors (321) from running, thereby avoiding excessive stretching of the fingers.

Furthermore, the active processing device (4) is further provided on a normal side of the rehabilitator's hand. The bending sensors (42) of the active processing device (4) are disposed on the fingers to detect a bending angle of the fingers. Then, the bending sensors (42) transmit the information including the bending angle to the second processing module (41), and the second processing module (41) further transmit the information to the first processing module (31) of the traction device (3), so the first processing module (31) can drive the driving motors (321) of the driving modules (32) to gradually rotate to the same angle as the detected bending angle of the normal side and make the rehabilitator's fingers on the affected side to stretch out by the guidance of the traction device (3). At the same time, the pressure sensors (34) of the traction device (3) also detect the flexural tension of the rehabilitator's fingers. When the first processing module (31) determines that the flexural tension exerted on the rehabilitator's fingers is greater than a predetermined value, the first processing module (31) transmits commands to the driving modules (32) to stop the driving motors (321) from running, thereby avoiding excessive stretching of the fingers.

Compared with the technique available now, the present invention has the following advantages:

1. The present invention having plural lower-support type of finger supports provide supports to carry the rehabilitator's fingers, so the rehabilitator can easily place his or her fingers on the first finger bases and the second finger bases.

2. The present invention has the traction device for providing tractions for the rehabilitator's fingers to stretch outwardly and can lift up the rehabilitator's fingers by the first finger bases and the second finger bases that are driven by the driving modules and the pulling ropes, so that the rehabilitator's fingers can be trained to stretch out and the activities of the rehabilitator's fingers on the affected side are gradually recovered.

3. The present invention further promotes the rehabilitation of the hand on the affected side with the hand on the normal side by the active processing device in signal connection to the traction device for acquiring the bending angle of the fingers on the normal side and driving the fingers on the affected side to bend at the same bending angle for rehabilitation.

What is claimed is:

1. A lower support rehabilitation device for fingers, comprising:
a cover plate having a hand covering portion and a plurality of through holes disposed on the hand covering portion;
a plurality of finger supports disposed at a bottom of the hand covering portion and each having a first finger base, a second finger base pivotally connected to the first finger base, and two side arms respectively disposed on two sides of the second finger base, wherein the first finger base is provided with a beam; and
a traction device disposed on the hand covering portion of the cover plate and having a first processing module, a plurality of driving modules electrically connected to the first processing module, a plurality of pulling ropes connected to the plurality of driving modules and a plurality of pressure sensors electrically connected to the first processing module, wherein each of the plurality of pulling ropes passes through one of the plurality of through holes for fixing to the beam of the first finger base.

2. The lower support rehabilitation device for fingers claimed in claim 1, wherein the hand covering portion comprises an arm covering portion, a hand back covering portion connected to the arm covering portion, a first finger covering portion connected to the hand back covering portion, and a second finger covering portion connected to the hand back covering portion.

3. The lower support rehabilitation device for fingers claimed in claim 2, comprises five finger supports, one of which is disposed at a bottom of the first finger covering portion and the other four are disposed at a bottom of the second finger covering portion.

4. The lower support rehabilitation device for fingers claimed in claim 1, wherein the cover plate is further provided with a plurality of motor fixed brackets and a plurality of pulling rope fixed brackets on the hand covering portion.

5. The lower support rehabilitation device for fingers claimed in claim 1, wherein the first finger base is further provided with a first lower pallet connected to the beam.

6. The lower support rehabilitation device for fingers claimed in claim 1, wherein the second finger base is provided with a second lower pallet and two side plates respectively disposed on two sides of the second lower pallet.

7. The lower support rehabilitation device for fingers claimed in claim 6, wherein each of the two side arms has a first end connected to each of the two side plates.

8. The lower support rehabilitation device for fingers claimed in claim 2, wherein each of the two side arms has a second end connected to a bottom of the first finger covering portion or to a bottom of the second finger covering portion.

9. The lower support rehabilitation device for fingers claimed in claim 1, wherein each of the plurality of driving modules comprises a driving motor and a swing arm connected to the driving motor for further connecting each of the plurality of pulling ropes.

10. The lower support rehabilitation device for fingers claimed in claim 1, further comprises an active processing device having a second processing module electrically connected to the first processing module and a plurality of bending sensors electrically connected to the second processing module.

* * * * *